United States Patent [19]

Sasaki

[11] Patent Number: 4,640,615
[45] Date of Patent: Feb. 3, 1987

[54] LIQUID REFRACTOMETER

[75] Inventor: Issei Sasaki, 15-402, Hanakawa-Cyuo-Danchi, 3-4, Hanakawa-kita 3-chome, Ishikari-machi, Ishikari-gun, Hokkaido, Japan

[73] Assignees: Issei Sasaki; Seiko Instruments & Electronics Ltd., both of Tokyo, Japan; a part interest

[21] Appl. No.: 660,923

[22] Filed: Oct. 15, 1984

[30] Foreign Application Priority Data

Oct. 20, 1983 [JP] Japan ................................. 58-197093

[51] Int. Cl.$^4$ ............................................. G01N 21/41
[52] U.S. Cl. ...................................... 356/130; 356/361
[58] Field of Search ......................... 356/128, 130, 361

[56] References Cited
U.S. PATENT DOCUMENTS 4,171,915 10/1979 Hesselink ............................. 356/361

FOREIGN PATENT DOCUMENTS

2120383 11/1983 United Kingdom ................ 356/361

Primary Examiner—F. L. Evans
Attorney, Agent, or Firm—Robert E. Burns; Emmanuel J. Lobato; Bruce L. Adams

[57] ABSTRACT

A liquid refractometer comprising a light source unit, a probe unit and a detection unit. The light source unit generates a beam of polarized mixed light composed of two coherent light waves that have been linearly polarized in directions at right angles to each other. The probe unit contains a polarization separation portion, a sample holding portion, a reference portion and a beam mixing portion. The polarization separation portion separates the mixed light beam back into the two polarized waves and directs one of the beams through the sample portion and the other beam through the reference portion. The mixing portion re-mixes the two waves after having passed through the sample holding portion and the reference portion. The detection unit receives the re-mixed light and measures the refractive index differences between the liquid sample and the reference portion. Fiber optics optically connect the light source unit, the probe unit and the detector unit.

27 Claims, 10 Drawing Figures

LIQUID REFRACTOMETER

BACKGROUND OF THE INVENTION

This invention provides means for measuring on a real time basis a refractive index by dipping directly a probe into a liquid whose refractive index is to be measured. The expected field of application of the present invention primarily includes the adjustment of a refractive index regulating solution and in the field using such a solution.

A refractometer using a refraction method is known as one of the conventional liquid refractometers. This refractometer measures the ratio of an angle of incidence to an angle of refraction at a boundary where the angle of refraction varies. A refractometer using a reflection method is also known. It measures a critical angle at which total reflection occurs at the boundary where the refractive index varies. This is a so-called "Abbe's refractometer". A refractometer using another reflection method determines the refractive index from the coefficient of reflection at the boundary where the refractive index varies.

However, the heretofore known methods described above provide measuring accuracy of refractive index which is as low as from $10^{-2}$ to $10^{-3}$, and hence cannot be used in the field requiring precise control of refractive index such as in the production of an optical communication fiber.

As one of the methods of precisely measuring the refractive index, a method using a so-called "interference method" is known. However, this method cannot measure the object to be measured on a real time basis. In order to control the production process of the optical fiber, the refractive index must be measured instantaneously with a high level of accuracy. Nonetheless, the conventional methods using the interference method essentially require sampling, and none of them can measure the refractive index in situ.

SUMMARY OF THE INVENTION

The present invention is directed to provide a liquid refractometer which eliminates the problems of the prior art described above and can precisely measure the refractive index of a liquid.

DETAILED DESCRIPTION OF THE INVENTION

Figure 1:
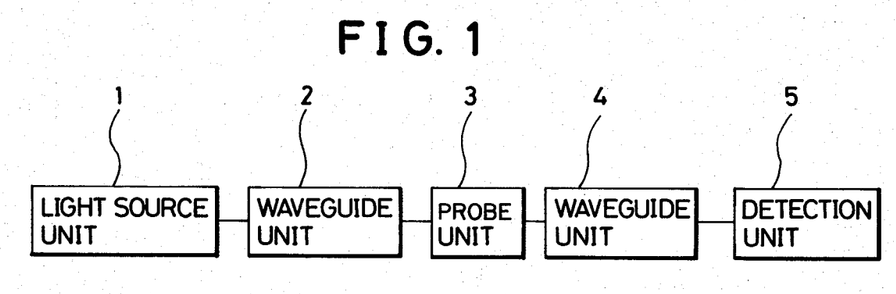
FIG. 1 is a block diagram of a liquid refractometer in accordance with the present invention.

The construction of the present invention is shown in FIG. 1. Reference numeral 1 represents a light source unit 1. In this light source unit 1, coherent light emitted from one light source is divided into two. After being linearly polarized in mutually crossing directions, these two polarized lights are mixed together (the mixed light will be hereinafter called "polarized mixed light"). This polarized mixed light propagates through a waveguide unit 2 and enters then a probe unit 3. After entering the probe unit 3, the polarized mixed light is divided into each linearly polarized light, and one of the polarized light waves passes through a sample liquid and the other passes through a reference medium. A phase difference or phase delay thus occurs between both polarized lights, and this phase difference is a function of the refractive index of the sample liquid. After generating the phase difference, the two polarized light waves are again mixed (hereinafter called "re-mixed wave) and are introduced into a detection unit 5 through a waveguide unit 4, and the phase difference is detected to determine the refractive index of the liquid.

As described above, the characterizing feature of the present invention resides in the arrangement in which the polarized mixed light is formed in the light source unit 1 and is then introduced into the probe unit 3, where it is separated, the polarized light waves pass respectively through the sample and the reference, and both polarized light waves are again mixed to form the mixed wave, which is then introduced into the detection unit 5 as the re-mixed wave for measurement. This method can measure the difference of the refractive indices between the sample and the reference on a real time basis.

The present invention forms a laser interferometer as a whole. However, the position of the light source is spaced apart from that of measurement because the present invention is based upon the premise that no sampling is effected, in particular, in order to supervise on the real time basis the liquid to be measured while it is being held in the state of use. Accordingly, the present invention first polarizes the two light waves to be interfered with each other in the directions crossing each other at right angles, and then mixes them together so as to bring them into the state where they behave as if they were one luminous flux. Thereafter, the present invention introduces the mixed wave to the measuring position that is the probe unit through the optical connecting means in the form of waveguide unit. This arrangement provides the advantage that any adverse influences due to disturbance are substantially offset and eliminated during interference. Morever, the probe unit is inserted into the measuring position.

This probe unit incorporates therein an optical system. In other words, the polarized mixed wave is separated spatially into the two original polarized lights depending upon the state of each polarized light. Apparently, one of the polarized waves passes through at least a part of the sample, while the other passes through the reference medium in the same way as in the ordinary interferometer. Next, these two polarized waves are again mixed and are then introduced into the detection unit. This eliminates any adverse influences due to disturbance in the same way as described above.

According to this optical arrangement, the light source unit 1, the probe unit 3 and the detection unit 5 can be connected by one optical fiber. As described above, it is the object of the present invention to measure the refractive index of the liquid, into which the probe is dipped, by use of the optical system that can utilize only a minute region inside the probe.

Figure 2:
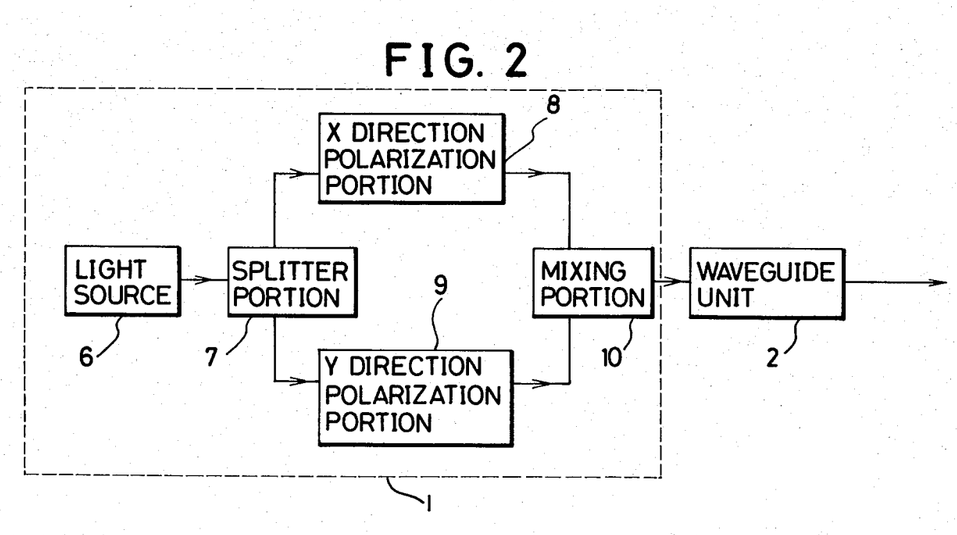
FIG. 2 is a detailed block diagram of a light source unit.

FIG. 2 shows in detail the light source unit 1. The light source 6 consists of a laser having coherence such that optical interference can be generated. The laser light is divided into two luminous flux by a splitter portion 7. A beam splitter or a prism is used as the splitter portion 7. Next, one of the light is turned into linearly polarized light by an X direction polarization portion 8. The X direction polarization portion 8 consists of a polarizer, for example. The other luminous flux is turned into a crossing linearly polarized wave by a Y direction polarization portion 9. The Y direction polarization portion 9 consists also a polarizer, for example. These two polarized waves that cross each other at right angles are mixed into one luminous flux by a mixing portion 10 and are then introduced into the waveguide unit 2. The waveguide unit 2 consists of optical fibers such as a multi-mode fiber, a single mode fiber, polarization wave preservation fiber, or the like.

Figure 3:
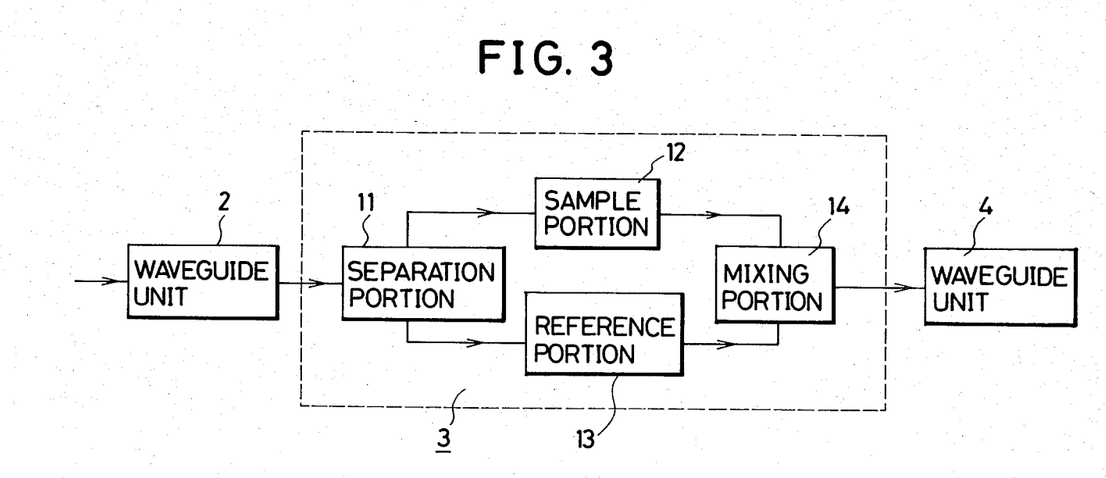
FIG. 3 is a detailed block diagram of a probe unit.

FIG. 3 shows in detail the probe unit 3.

The polarized mixed wave that is guided by the waveguide unit 2 is separated into the original, mutually crossing polarized waves by a polarization separation portion 11. The separation portion 11 consists of a split type analyzer, for example. One of the polarized waves passes through a sample holding portion 12. The probe 3 is dipped into the sample liquid to hold the sample liquid in the sample portion 12 in order to introduce the sample for measurement. The other polarized wave passes through a reference portion. The reference portion 13 consists of refractive-index-known material such as quartz whose refractive index is known in advance, for example. Therefore, the refractive index of the liquid is given as the difference with that of quartz as the reference material, in the refractometer of the present invention.

Originally, a sample temperature must be pre-known when measuring a refractive index. In the present invention, however, the refractive index of a liquid can be measured with a high level of accuracy as the difference with the refractive index of the reference medium (e.g., quartz) under a given temperature condition. Hence, the present invention is more convenient in practice.

After passing through the mutually different media, the polarized light waves generate the phase difference. They are then turned into one luminous flux by the mixing portion 14 and are thereafter introduced into the detection unit 5 through the waveguide unit 4. The characteristic of the re-mixed two linearly polarized light waves caused by the laser interference is measured there and the desired refractive index is determined.

Here, three different principles for the measurement of laser interference will be described.

The relation between an interference output signal and the difference of refractive indices between two media (sample and reference) can be expressed by the following formula:

(1) When the two coherent light have the same frequency (in the case of homodyne):

$$I = \mu I_o [1 + \cos(K n_S X_S - K n_R X_R)] \quad (1)$$

where I is the output signal, $\mu$ is the efficiency of the detector, $I_o$ is a total average power of light, K is the number of waves of the light used ($K = 2\pi\lambda$, $\lambda$ is the wavelength of the light in vacuum), X is the occupying length of the medium in the optical path length, n is the refractive index of the medium, and S and R are the suffix of the sample and the reference medium, respectively.

If $n_R X_S - n_R X_R = \pi/2$ can be put into the formula (1), the change of the output due to a delicate change of the refractive index $\Delta n = n_S - n_R$ can be approximated as follows:

$$\Delta I \cong I_i K \Delta n X_S \quad (2)$$

Symbol $I_i$ represents the magnitude of the output when $n_R X_S - n_R X_R = \pi/2$ is set. In this manner, $\Delta n$ can be obtained by knowing K and $X_S$ and measuring $\Delta I$.

(2) When the two coherent light have mutually different frequencies $\alpha_1$ and $\alpha_2$ (in the case of heterodyne): When an AC component is considered:

$$I = \mu I_o \cdot \cos(2\pi \Delta f \, t n_S X_S - n_R X_R) \quad (3)$$

where $\Delta \alpha = |\alpha_1 - \alpha_2|$

When the phase of a carrier wave having a frequency $\Delta f$ which does not entirely depend upon the amplitude component of the cos wave is taken into consideration in the formula (3), the delicate refractive index $\Delta n$ can be grasped as the phase change $\Delta \phi = \Delta n X R$ ($X = X_S = X_R$). Since approximation and initial setting that are necessary in the homodyne of the formula (2) are not necessary in this case, measurement can be made with a higher level of accuracy.

Besides the two interference measuring methods described above, there is a third method. This method uses elliptic polarization. When mutually crossing polarized light waves are incident to two optical paths of an interferometer, the state of polarization of the interference wave becomes different due to the phase difference. If the phase difference is 0°, linearly polarized light (with an angle of polarization of 45°) is provided, and if the phase difference is 90°, circularly polarized light is provided. If the phase difference is between 0° and 90°, the state referred to as the "elliptic polarization" is provided. Therefore, the difference of the refractive indices described above can be determined by measuring the ellipticity angle of polarization of the polarized light. The present invention can utilize all the three principles described above.

[Embodiment 1]

Figure 4:
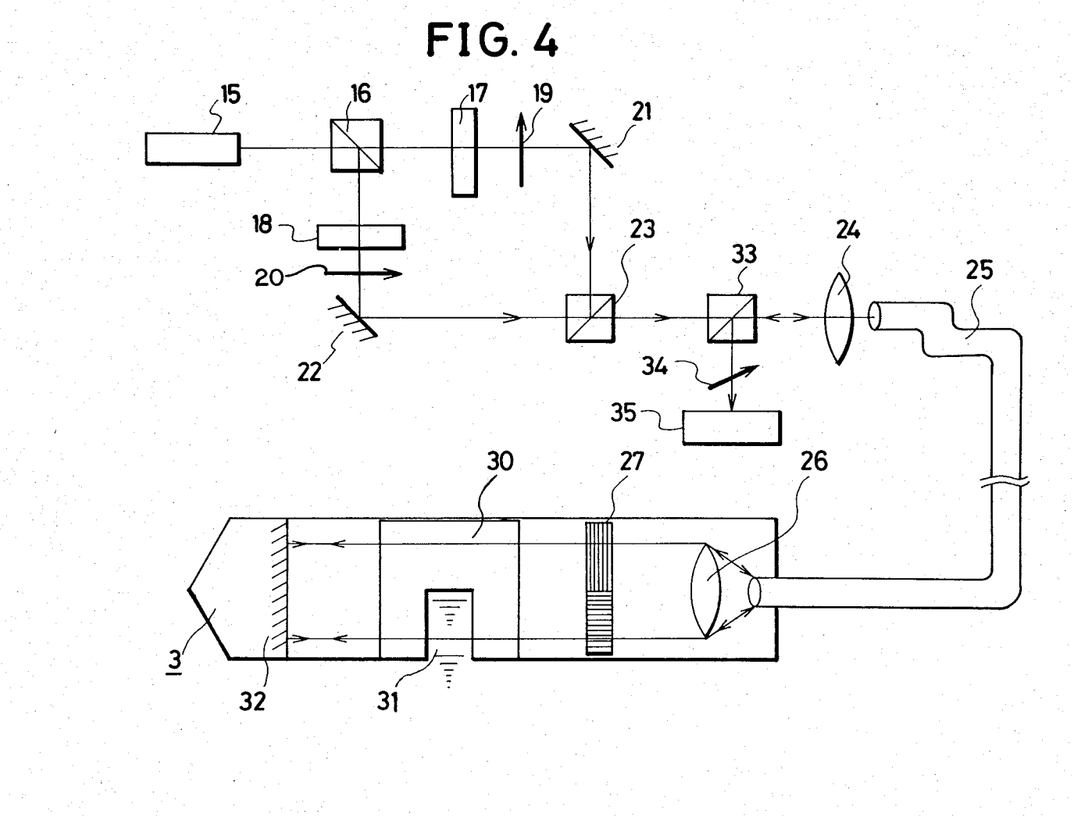
FIG. 4 is a block diagram showing one embodiment of the present invention.

FIG. 4 shows Embodiment 1 of the present invention using the heterodyne method. The light source 15 is laser and emits coherent light. The light source may be a subcoherent light source. The coherent light is split into two luminous flux by the splitter 16. These two luminous flux originally have a frequency $\alpha_o$, but are frequency-modulated to $\alpha_1$ and $\alpha_2$ by optical modulators 17 and 18, respectively. Bragg call or Raman-Nath call is used as the modulator. These luminous flux $\alpha_1$ and $\alpha_2$ are converted to polarized light waves that cross each other at right angles, that is, X polarized light wave and Y polarized light waves, by the polarizers 19 and 20, respectively. After their directions are changed by the mirrors 21 and 22, the two polarized light waves are mixed into one luminous flux, that is, the mixed polarized light wave, by the optical mixer 23.

The polarized mixed wave is coveraged by a convex lens 24 into the incident port of the optical fiber 25 and is then introduced into the interior of the optical fiber 25. The optical fiber 25 plays the role of the waveguide unit 2 and introduces the polarized mixed wave into the probe unit 3.

Figures 5, 6, 7:
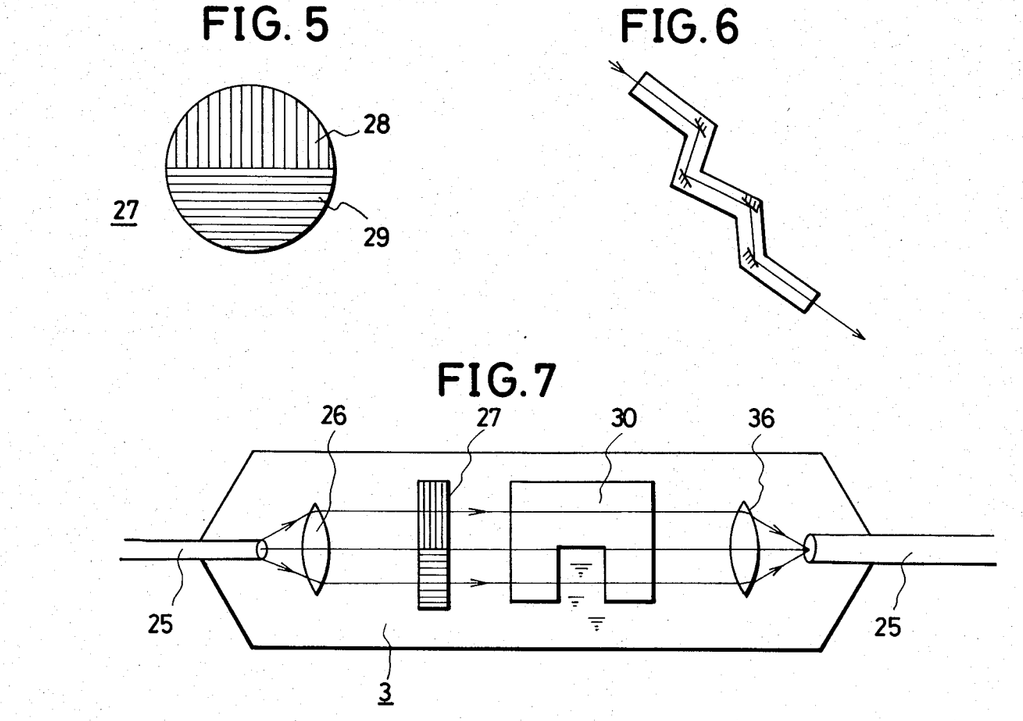
FIGS. 5, 6, 9 and 10 show the components used for the embodiment of the present invention.
FIGS. 7 and 8 are schematic views of the probe units used for other embodiments of the present invention.

After passing through the optical fiber 25, the polarized mixed wave diverges from the output of the optical fiber 25 and is turned into parallel rays by a microlens 26. As the parallel rays pass through a split type analyzer 27, the analyzer 27 separates the mixed waves of the polarized luminous flux into the polarized light waves which cross each other at right angles. This split type analyzer 27 has a construction such as shown in FIG. 5. It consists of two semi-circular analyzer elements 28 and 29 that have the axes of polarization crossing each other at right angles, and are bonded to each other. The upper half of the polarized mixed wave passing through the split type analyzer 27 contains only the polarized light wave that oscillates in the Y direction, while the lower half contains only the polarized light wave that oscillates in the X direction. Therefore, the polarized mixed light wave emitted from the light source unit is separated by the split type analyzer 27.

In other words, the split type analyzer 27 separates the mixed wave of the X polarized light wave having the frequency $\alpha_1$ and the Y polarized light wave having the frequency $\alpha_2$ into the original X polarized light wave having the frequency $\alpha_1$ and to the original Y polarized light wave having the frequency $\alpha_2$.

Next, the X polarized light wave of the frequency $\alpha_1$ thus separated passes through the sample liquid that is introduced into the recess 31 of the sample holding portion 30 made of quartz. The sample liquid is automatically introduced into the recess 31 when the probe 3 is dipped as a whole into the liquid.

The Y polarized light of the frequency $\alpha_2$ thus separated passes through the thick portion of quartz among the sample holding portion 30. This thick portion serves as the reference portion because it has a known refractive index nR. When the total optical path of the rays of light of the frequency $\alpha_1$ is compared with that of the rays of light of the frequency $\alpha_2$, they are different only at the sample and reference portions inside the probe unit, and the rest are common. The phase delay of the rays of light of the frequency $\alpha_1$ occurs because the rays pass through the sample. The difference of refractive index $\Delta n$ of the sample liquid relative to the reference portion can be determined by detecting this phase delay.

The relation of the phase delay $\Delta\phi$ and the difference of refractive index $\Delta n$ is given by $\Delta\phi=2xk\Delta n$. The method of detecting the phase delay $\Delta\phi$ will be explained elsewhere.

The light passing through the sample holding portion 30 is reflected in the opposite direction by the mirror 32 disposed ahead, and travels on the same optical path as the coming light path but in the opposite direction. The light passing reversely through the split type analyzer 27 is re-mixed by the microlens 26, and returns as the re-mixed light wave through the optical fiber 25. In this manner, the waveguide unit 2 and the waveguide unit 4 in this embodiment are composed of the common optical fiber 25. The re-mixed light wave that passes reversely the optical fiber passes through the convex lens 24, is turned into the parallel rays and is thereafter picked up by the beam splitter 33. After the parallel rays pass through the analyzer 34, that is set to an angle of 45° relative to the polarizing direction of the re-mixed light wave, they are introduced into the detector 35. The operation of the detector 35 will be next described.

The re-mixed light wave as the mixed light waves of the polarized light waves having the frequencies $\alpha_1$ and $\alpha_2$ pass through the analyzer 34 that is set to the angle of 45° relative to the polarizing direction of the re-mixed light wave, so that the component of each polarized light in the polarizing direction of the analyzer is picked up, and these components interfere with each other.

In the laser interference method (heterodyne system) using the interference of the two rays of light having the mutually different frequencies $\alpha_1$ and $\alpha_2$, the waveform of the output signal of the interference wave is a sine wave having a frequency $(\alpha_1-\alpha_2)$, and contains $\Delta\phi$ as the phase difference component. Therefore, the phase difference $\Delta\phi$ can be determined by comparing the output signal with the reference signal by the detector 35 consisting of the phase detection circuit 35. Therefore, $\Delta n$ can be obtained from the formula $\Delta\phi=2xk\Delta n$.

[Other Embodiments]

Though Embodiment 1 uses the heterodyne system as the interference system, other methods such as the homodyne system or the system using elliptic polarization described earlier may be used, in principle. In such a case, the construction of Embodiment 1 shown in FIG. 4 can be used substantially as such except that the optical modulators 17 and 18 are not necessary. In Embodiment 1, the beam splitter 16 and the analyzers 19 and 20 from the mutually crossing polarized light waves, but the beam splitter 16 and the analyzers 19 and 20 can be substituted by a beam splitter having the capacity of separating the polarized light.

A Wollaston prism or the like can be used in place of the beam splitters 16 and 23.

Though Embodiment 1 uses the optical fiber in order to guide the polarized mixed wave to the probe unit, an optical path having flexibility and a plurality of mirror surfaces such as shown in FIG. 6 can be used in other embodiments of the invention.

In Embodiment 1, the waveguide unit 2 is used also as the waveguide unit 4, but they may of course be separate as shown in FIG. 7. In such a case, the polarized mixed wave is turned into parallel rays by the microlens 26, and is then separated by the split type analyzer, and the rays of light pass separately through the sample liquid of the sample holding portion and the reference portion. Finally, they are converged by the microlens 36, and are guided to the detection unit through the other optical fiber 25.

Figure 8:
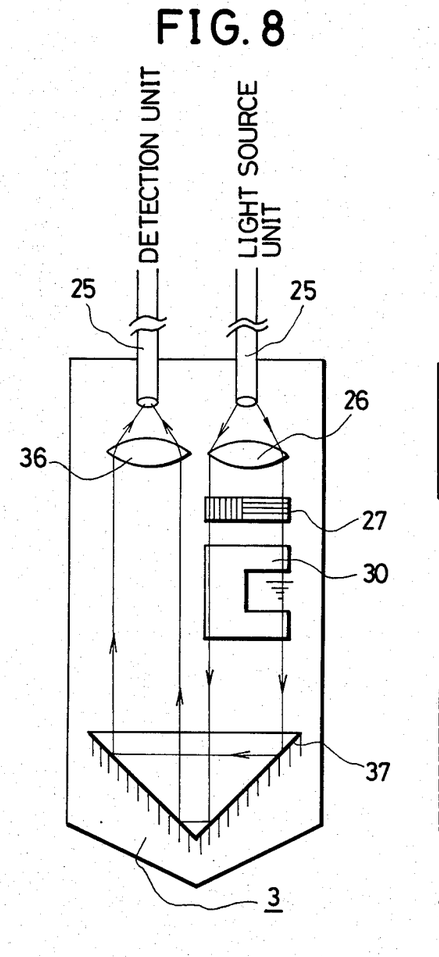

In the embodiment described above, the coming direction of the light is the same as the returning direction, but they may be opposite by use of a rectangular prism as shown in FIG. 8.

In Embodiment 1, the polarization separation element 27 used for the probe unit 3 may be SELFOC lens (trademark), for example.

The polarization separation element 27 used for the probe unit 3 in Embodiment 1 is a wave front split type analyzer, but a beam splitter having the function of polarization and separation may be used in other embodiments of the invention.

Figure 9:
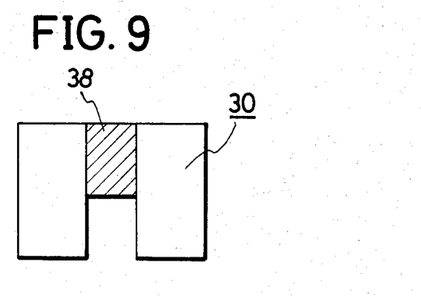

The sample holding unit 30 in Embodiment 1 has a unitary structure including the reference portion. In other embodiments of the invention, however, the reference portion 38 may be of a cassette type such as shown in FIG. 9 so that a variety of reference materials can be used.

Embodiment 1 uses the polarization surface preservation optical fiber as the waveguide units 2 and 4. In other embodiments of the invention, however, those optical fibers in which the polarization surface rotates may also be used. In such a case, however, it is necessary that the set angle of the polarization separation element is vaiable with respect to the section of the optical fiber in the probe unit so that it can be adjustable during measurement. Alternatively, the optical fiber 25 may be rotated and adjusted on the contrary, with the set angle of the polarization separation element being kept fixed.

Figure 10:
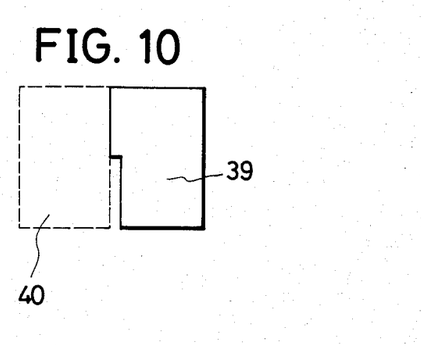

FIG. 10 depicts a reference medium chip 39 to be used when the gap must be extremely small. This is prepared by bonding two small chips having slightly different thickness to each other, or by partial polishing. (In this case, a part is replaced by the liquid; see 40 in FIG. 10). The other construction is exactly the same as that shown in FIG. 9.

[Effect of the Invention]

As described above, the present invention can provide a high precision real time (in situ) type liquid refractometer which can measure a refractive index on a real time basis by dipping a probe unit into a liquid to be measured, while utilizing a high precision measurement method of refractive index in accordance with a laser interference method.

What is claimed is:

1. A liquid refractometer comprising: a light source unit for generating a polarized mixed light composed of two coherent light waves that have been polarized in directions crossing each other at right angles; a probe unit having a sample holding portion for holding a liquid sample, a reference portion, polarization separation means for separating said polarized mixed light back to the two polarized light waves and for propagating one of the two waves through said sample holding portion and propagating the other of the two waves through said reference portion, and means for re-mixing the two waves after propagation thereof through said sample holding portion and said reference portion; a detection unit for effecting measurement of the refractive index difference between the liquid sample and the reference portion upon receiving the re-mixed light; and light guide means for optically connecting said light source, probe unit and detection unit.

2. The liquid refractometer as defined in claim 1; wherein said light source unit includes means for generating a polarized mixed light wave composed of two light waves having mutually different frequencies, and said detection unit includes an optical heterodyne detection system for measuring the refractive index difference.

3. The liquid refractometer as defined in claim 1; wherein said light guide means comprises an optical fiber for guiding said polarized mixed light wave from the light source unit to said probe unit.

4. The liquid refractometer as defined in claim 1; wherein said light guide means comprises means defining an optical path having a plurality of mirror surfaces and flexibility for guiding said polarized mixed light wave from the light source unit to said probe unit.

5. The liquid refractometer as defined in claim 3; wherein said optical fiber for guiding said polarized mixed light wave to said probe unit is used also as an optical fiber for guiding said re-mixed light from the probe unit to the detection unit.

6. The liquid refractometer as defined in claim 1; wherein the polarization separation means in said probe unit comprises a wave front split-type analyzer.

7. The liquid refractometer as defined in claim 1; wherein the polarization separation means in said probe unit comprises a beam splitter having the functions of polarization and separation.

8. The liquid refractometer as defined in claim 1; wherein said probe unit further comprises a reflecting mirror or a prism disposed at the tip of the optical path of said two polarized light waves separated spatially from each other in said probe unit in order to invert their travelling direction.

9. The liquid refractometer as defined in claim 1; wherein said probe unit further comprises an optical system including a microlens disposed on the optical path so as to convert the rays of light into parallel rays or to converge the same.

10. The liquid refractometer as defined in claim 1; wherein said reference portion of the probe unit comprises a medium chip disposed at an uncommon portion on the optical paths of two polarized light waves separated spatially from each other in said probe unit, while said sample holding portion is disposed at the other part of said uncommon portion of the optical paths, and the rest of the optical paths consist of a common medium.

11. The liquid refractometer as defined in claim 1; wherein if said polarized mixed light wave is originally a circularly polarized light wave or a synthetic linearly polarized light wave, said detection unit decides the degree of ellipticity of the polarized light so as to determine the difference of refractive index between the sample liquid and reference portion.

12. The liquid refractometer as defined in claim 2; wherein said light source unit includes means for generating said polarized mixed light wave synthesized from two light waves having mutually different frequencies; and said detection unit includes means for producing a signal representative of the difference frequency by an optical heterodyne method and for analyzing the phase of said signal so as to determine the refractive index of the propagation sample medium.

13. The liquid refractometer as defined in claim 1; wherein a set angle of said polarization separation means of said probe unit is variable and can be regulated at the time of measurement so that measurement can be made at an optimal value.

14. The liquid refractometer as defined in claim 1; wherein the angle of polarization of the light incident to said polarization separation means of said probe unit is variable so that measurement can be made at an optimal value.

15. A liquid refractometer comprising:
a light source unit for generating a mixed polarized light wave composed of two linearly polarized light waves the polarization directions of which cross each other at right angles;
a probe unit having a sample holding portion for holding a sample liquid during use of the liquid refractometer, a reference portion made of a reference material of known refractive index, polarization separation means optically coupled to the light source unit for separating the mixed polarized light wave into the two linearly polarized light waves and for directing one linearly polarized light wave through the sample holding portion and directing the other linearly polarized light wave through the reference portion, and means for re-mixing the two linearly polarized light waves after the two linearly polarized light waves pass through the sample holding portion and the reference portion; and
a detection unit optically coupled to the probe unit for detecting a characteristic of the re-mixed two linearly polarized light waves which bears information representative of the difference of refractive index between the sample liquid and the reference material.

16. A liquid refractometer as defined in claim 15 further comprising connecting means for optically connecting the light source unit, the probe unit and the detection unit.

17. A liquid refractometer as defined in claim 15; wherein said light source unit includes means for generating a polarized mixed light wave composed of two linearly polarized waves having different frequencies; and said detection unit includes means for detecting a phase delay between the re-mixed two linearly polarized means which is proportional to the refractive index difference between the sample liquid and the reference material.

18. A liquid refractometer as defined in claim 15; wherein said light source unit includes means for generating a circularly or synthetic linearly polarized light wave; and said detection unit includes means for detecting the degree of ellipticity of the re-mixed two linearly polarized waves which corresponds to the refractive index difference between the sample liquid and the reference material.

19. A liquid refractometer as defined in claim 15; wherein the polarization separation means comprises a wave front split-type analyzer.

20. A liquid refractometer as defined in claim 15; wherein the polarization separation means comprises a beam splitter operative to effect polarization and separation of light waves.

21. A liquid refractometer as defined in claim 15; wherein said probe unit further includes means disposed along the optical paths of the two linearly polarized light waves for reversing the directions of travel thereof after the two linearly polarized light waves pass through the sample holding portion and the reference portion.

22. A liquid refractometer as defined in claim 15; wherein said probe unit includes an optical system for converting the light waves into parallel rays or for converging the parallel rays depending on the direction of travel thereof.

23. A liquid refractometer as claimed in claim 15; wherein the reference portion of the probe unit comprises a reference medium chip disposed at an uncommon portion on the optical paths of the two polarized light waves separated spatially from each other in said probe unit, the sample holding portion being disposed at another part of the uncommon portion of the optical paths.

24. A liquid refractometer as defined in claim 16; wherein the connecting means comprises an optical fiber.

25. A liquid refractometer as defined in claim 16; wherein the connecting means comprises means defining a flexible optical path having a plurality of mirror surfaces.

26. A liquid refractometer as defined in claim 24; wherein the optical fiber comprises a single optical fiber commonly connecting the light source unit and the probe unit as well as the probe unit and the detection unit.

27. A method for measuring the refractive index of a liquid, comprising the steps of:
generating a mixed polarized light wave composed of two linearly polarized light waves the polarization directions of which cross each other at right angles;
separating the mixed polarized light wave into said two linearly polarized light waves;
passing one linearly polarized light wave through a sample liquid held in a sample holding portion of a probe unit by dipping the probe unit into the sample liquid while passing the other linearly polarized light wave through a reference material of known refractive index material provided in the probe unit;
re-mixing the two linearly polarized light waves after the same have passed through the sample liquid and the reference material; and
detecting a characteristic of the two re-mixed linearly polarized light waves which bears information representative of the refractive index difference between the sample liquid and the reference material.

* * * * *